United States Patent
Babiel et al.

(10) Patent No.: US 9,447,476 B2
(45) Date of Patent: Sep. 20, 2016

(54) METHOD FOR PREVENTING HIGH MOLECULAR WEIGHT PRODUCTS DURING AMPLIFICATION

(71) Applicant: Roche Molecular System, Inc., Pleasanton, CA (US)

(72) Inventors: Reiner Babiel, Seehausen (DE); Frank Bergmann, Iffeldorf (DE); Dorothea Sizmann, Iffeldorf (DE)

(73) Assignee: Roche Molecular Systems, Inc., Pleasanton, CA (US)

(*) Notice: Subject to any disclaimer, the term of this patent is extended or adjusted under 35 U.S.C. 154(b) by 0 days.

(21) Appl. No.: 14/055,090

(22) Filed: Oct. 16, 2013

(65) Prior Publication Data
US 2014/0113279 A1 Apr. 24, 2014

Related U.S. Application Data

(60) Provisional application No. 61/715,464, filed on Oct. 18, 2012.

(30) Foreign Application Priority Data

Oct. 18, 2012 (EP) .................................... 12189009

(51) Int. Cl.
| C12Q 1/68 | (2006.01) |
| C12Q 1/70 | (2006.01) |
| C07H 21/02 | (2006.01) |

(52) U.S. Cl.
CPC .............. *C12Q 1/707* (2013.01); *C12Q 1/686* (2013.01); *C12Q 1/6844* (2013.01); *C12Q 1/6848* (2013.01); *C12Q 1/6853* (2013.01)

(58) Field of Classification Search
CPC .................. C12Q 2525/161; C12Q 2525/173; C12Q 2531/113; C12Q 1/6844; C12Q 1/6848; C12Q 1/6853; C12Q 1/686
See application file for complete search history.

(56) References Cited

U.S. PATENT DOCUMENTS

| 4,683,195 | A | | 7/1987 | Mullis et al. | |
| 4,683,202 | A | | 7/1987 | Mullis | |
| 5,001,050 | A | * | 3/1991 | Blanco et al. | ................... 435/5 |
| 5,210,015 | A | | 5/1993 | Gelfand et al. | |
| 5,487,972 | A | | 1/1996 | Gelfand et al. | |
| 5,498,392 | A | * | 3/1996 | Wilding et al. | ............. 422/68.1 |
| 6,465,241 | B2 | * | 10/2002 | Haronian et al. | .......... 435/287.2 |
| 6,716,580 | B2 | * | 4/2004 | Gold et al. | ................... 435/6.12 |
| 2004/0110182 | A1 | | 6/2004 | Koizumi et al. | |
| 2009/0291475 | A1 | | 11/2009 | Lao et al. | |

FOREIGN PATENT DOCUMENTS

| EP | 12189009 | 2/2013 |
| EP | 13189020 | 11/2013 |
| WO | WO9513399 | 5/1995 |
| WO | WO0194638 | 12/2001 |
| WO | WO03062445 | 7/2003 |
| WO | 2004081225 A2 | 9/2004 |
| WO | 2006135765 A1 | 12/2006 |
| WO | WO2006135765 | 12/2006 |
| WO | 2008064687 A1 | 6/2008 |
| WO | 2012032510 A1 | 3/2012 |

OTHER PUBLICATIONS

Afonia, Irina, et al., 2007, "Primers with 5' flaps improve real-time PCR", Biotechniques, 43(6):770-774.
Liu, Qiang, et al. 1997, "Overlapping PCR for Bidirectional PCR Amplification of Specific Alieles: A Rapid One-Tube Method for Simultaneously Differentiating Homozygotes and Heterozygotes", Genome Research, 7:389-398.
Longo, Mary C., et al., 1990, "Use of uracil DNA glycosylase to control carry-over contamination in polymerase chain reactions", Gene, 93:125-128.
Afonina et al., Primers with 5' flaps improve real-time PCR, Biotechniques vol. 43(3) (2007), p. 1-3.
Hymas, Weston C., 2010, "Development of a multiplex real-time RT-PCR assay for detection of influenza A, influenza B, RSV and typing of the 2009-H1N1 influenza virus", Journal of Virological Methods, 167:113-118.

* cited by examiner

*Primary Examiner* — Teresa E Strzelecka
(74) *Attorney, Agent, or Firm* — Eric Grant Lee; Jeff Bernhardt

(57) ABSTRACT

The present invention is directed to improved methods for amplifying and detecting a nucleic acid target that may be present in a biological sample comprising a primer pair for generating an amplicon, wherein at least one primer is modified at the 5' terminus with a polyN sequence being non-complementary to the target sequence, and a detectable probe specific for said amplicon or a DNA binding dye. The formation of high molecular weight products during amplification is prevented or partly or completely suppressed. The invention further provides reaction mixtures and kits comprising said primers for preventing or suppressing the formation of high molecular weight products during amplification and detection of the nucleic acid target.

17 Claims, 5 Drawing Sheets

Reference primers:
 5` - GCAGAAAGCGTCTAGCCATGGCGTTA - 3` (SEQ ID NO: 1)
 5` - GCAAGCACCCTATCAGGCAGTACCACAA - 3` (SEQ ID NO: 2)

modG2 overhang variants:
 5` - GGGCAGAAAGCGTCTAGCCATGGCGTTA - 3` (SEQ ID NO: 13)
 5` - GGGCAAGCACCCTATCAGGCAGTACCACAA - 3` (SEQ ID NO: 14)

30 and 40 cycles　　　　　50 and 60 cycles modT4 overhang variants:
 5` - TTTTGCAGAAAGCGTCTAGCCATGGCGTTA - 3` (SEQ ID NO: 9)
 5` - TTTTGCAAGCACCCTATCAGGCAGTACCACAA - 3` (SEQ ID NO: 10)

30 and 40 cycles      50 and 60 cycles modA4 overhang variants:
 5` - AAAAGCAGAAAGCGTCTAGCCATGGCGTTA - 3` (SEQ ID NO: 3)
 5` - AAAAGCAAGCACCCTATCAGGCAGTACCACAA - 3` (SEQ ID NO: 4)

60 cycles   50 cycles      40 cycles   30 cycles modA6 overhang variants:
   5` - AAAAAAGCAGAAAGCGTCTAGCCATGGCGTTA - 3` (SEQ ID NO: 5)
   5` - AAAAAAGCAAGCACCCTATCAGGCAGTACCACAA - 3` (SEQ ID NO: 6)

30 cycles 40 and 50 cycles 60 cycles modA8 overhang variants:
    5` - AAAAAAAAGCAGAAAGCGTCTAGCCATGGCGTTA - 3` (SEQ ID NO: 7)
    5` - AAAAAAAAGCAAGCACCCTATCAGGCAGTACCACAA - 3` (SEQ ID NO: 8)

30 and 40 cycles         50 and 60 cycles mod(AT)2 overhang variants:
    5` - ATATGCAGAAAGCGTCTAGCCATGGCGTTA - 3` (SEQ ID NO: 15)
    5` - ATATGCAAGCACCCTATCAGGCAGTACCACAA - 3` (SEQ ID NO: 16)

30 and 40 cycles         50 and 60 cycles mixedN6 overhang variants:
5` - GACTTAGCAGAAAGCGTCTAGCCATGGCGTTA - 3` (SEQ ID NO: 17)
5` - CTCTAAGCAAGCACCCTATCAGGCAGTACCACAA - 3` (SEQ ID NO: 18)

30 and 40 cycles       50 and 60 cycles

SEQUENCE LISTING

<160> NUMBER OF SEQ ID NOS: 32

<210> SEQ ID NO 1
<211> LENGTH: 26
<212> TYPE: DNA
<213> ORGANISM: Artificial sequence
<220> FEATURE:
<223> OTHER INFORMATION: Synthetic primer

<400> SEQUENCE: 1
gcagaaagcg tctagccatg gcgtta              26

<210> SEQ ID NO 2
<211> LENGTH: 28
<212> TYPE: DNA
<213> ORGANISM: Artificial Sequence
<220> FEATURE:
<223> OTHER INFORMATION: Synthetic primer

<400> SEQUENCE: 2
gcaagcaccc tatcaggcag taccacaa              28

<210> SEQ ID NO 3
<211> LENGTH: 30
<212> TYPE: DNA
<213> ORGANISM: Artificial Sequence
<220> FEATURE:
<223> OTHER INFORMATION: Synthetic primer

<400> SEQUENCE: 3
aaaagcagaa agcgtctagc catggcgtta              30

<210> SEQ ID NO 4
<211> LENGTH: 32
<212> TYPE: DNA
<213> ORGANISM: Artificial Sequence
<220> FEATURE:
<223> OTHER INFORMATION: Synthetic primer

<400> SEQUENCE: 4
aaaagcaagc accctatcag gcagtaccac aa              32

<210> SEQ ID NO 5
<211> LENGTH: 32
<212> TYPE: DNA
<213> ORGANISM: Artificial Sequence
<220> FEATURE:
<223> OTHER INFORMATION: Synthetic primer

<400> SEQUENCE: 5
aaaaaagcag aaagcgtcta gccatggcgt ta              32

<210> SEQ ID NO 6
<211> LENGTH: 34
<212> TYPE: DNA
<213> ORGANISM: Artificial Sequence
<220> FEATURE:
<223> OTHER INFORMATION: Synthetic primer

<400> SEQUENCE: 6
aaaaaagcaa gcaccctatc aggcagtacc acaa              34

<210> SEQ ID NO 7
<211> LENGTH: 34
<212> TYPE: DNA
<213> ORGANISM: Artificial Sequence
<220> FEATURE:
<223> OTHER INFORMATION: Synthetic primer

<400> SEQUENCE: 7
aaaaaaaagc agaaagcgtc tagccatggc gtta              34

<210> SEQ ID NO 8
<211> LENGTH: 36
<212> TYPE: DNA

```
<213> ORGANISM: Artificial Sequence
<220> FEATURE:
<223> OTHER INFORMATION: Synthetic primer

<400> SEQUENCE: 8
aaaaaaaagc aagcacccta tcaggcagta ccacaa                              36

<210> SEQ ID NO 9
<211> LENGTH: 30
<212> TYPE: DNA
<213> ORGANISM: Artificial Sequence
<220> FEATURE:
<223> OTHER INFORMATION: Synthetic primer

<400> SEQUENCE: 9
ttttgcagaa agcgtctagc catggcgtta                                     30

<210> SEQ ID NO 10
<211> LENGTH: 32
<212> TYPE: DNA
<213> ORGANISM: Artificial Sequence
<220> FEATURE:
<223> OTHER INFORMATION: Synthetic primer

<400> SEQUENCE: 10
ttttgcaagc accctatcag gcagtaccac aa                                  32

<210> SEQ ID NO 11
<211> LENGTH: 32
<212> TYPE: DNA
<213> ORGANISM: Artificial Sequence
<220> FEATURE:
<223> OTHER INFORMATION: Synthetic primer

<400> SEQUENCE: 11 tttttgcag aaagcgtcta gccatggcgt ta                                   32

<210> SEQ ID NO 12
<211> LENGTH: 34
<212> TYPE: DNA
<213> ORGANISM: Artificial Sequence
<220> FEATURE:
<223> OTHER INFORMATION: Synthetic primer

<400> SEQUENCE: 12 tttttgcaa gcaccctatc aggcagtacc acaa                                 34

<210> SEQ ID NO 13
<211> LENGTH: 28
<212> TYPE: DNA
<213> ORGANISM: Artificial Sequence
<220> FEATURE:
<223> OTHER INFORMATION: Synthetic primer

<400> SEQUENCE: 13
gggcagaaag cgtctagcca tggcgtta                                       28

<210> SEQ ID NO 14
<211> LENGTH: 30
<212> TYPE: DNA
<213> ORGANISM: Artificial Sequence
<220> FEATURE:
<223> OTHER INFORMATION: Synthetic primer

<400> SEQUENCE: 14
gggcaagcac cctatcaggc agtaccacaa                                     30
```

<210> SEQ ID NO 15
<211> LENGTH: 30
<212> TYPE: DNA
<213> ORGANISM: Artificial Sequence
<220> FEATURE:
<223> OTHER INFORMATION: Synthetic primer

<400> SEQUENCE: 15
atatgcagaa agcgtctagc catggcgtta                                    30

<210> SEQ ID NO 16
<211> LENGTH: 32
<212> TYPE: DNA
<213> ORGANISM: Artificial Sequence
<220> FEATURE:
<223> OTHER INFORMATION: Synthetic primer

<400> SEQUENCE: 16
atatgcaagc accctatcag gcagtaccac aa                                 32

<210> SEQ ID NO 17
<211> LENGTH: 32
<212> TYPE: DNA
<213> ORGANISM: Artificial Sequence
<220> FEATURE:
<223> OTHER INFORMATION: Synthetic primer

<400> SEQUENCE: 17
gacttagcag aaagcgtcta gccatggcgt ta                                 32

<210> SEQ ID NO 18
<211> LENGTH: 34
<212> TYPE: DNA
<213> ORGANISM: Artificial Sequence
<220> FEATURE:
<223> OTHER INFORMATION: Synthetic primer

<400> SEQUENCE: 18
ctctaagcaa gcaccctatc aggcagtacc acaa                               34

<210> SEQ ID NO 19
<211> LENGTH: 24
<212> TYPE: DNA
<213> ORGANISM: Artificial Sequence
<220> FEATURE:
<223> OTHER INFORMATION: Synthetic primer

<400> SEQUENCE: 19
aaaaaaccca ctctatgtcc ggtc                                          24

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
aaatggcgtc tcccacgcgg ctgg                                          24

<210> SEQ ID NO 21
<211> LENGTH: 27
<212> TYPE: DNA
<213> ORGANISM: Artificial Sequence
<220> FEATURE:

<223> OTHER INFORMATION: Synthetic primer

<400> SEQUENCE: 21
atatatgtac gccggaattg ccggaaa                                       27

<210> SEQ ID NO 22
<211> LENGTH: 27
<212> TYPE: DNA
<213> ORGANISM: Artificial Sequence
<220> FEATURE:
<223> OTHER INFORMATION: Synthetic primer

<400> SEQUENCE: 22 atatatctttt ccccaggacc tgccggt                                      27

<210> SEQ ID NO 23
<211> LENGTH: 21
<212> TYPE: DNA
<213> ORGANISM: Artificial Sequence
<220> FEATURE:
<223> OTHER INFORMATION: Synthetic primer

<400> SEQUENCE: 23
aaacccactc tatgtccggt c                                             21

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
tggcgtctcc cacgcggctg g                                             21

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
gtacgccgga attgccggaa a                                             21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
ctttccccag gacctgccgg t                                             21

<210> SEQ ID NO 27
<211> LENGTH: 21
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 6-carboxy-fluorescein-dC
<220> FEATURE:
<221> NAME/KEY: modified_base

```
<222> LOCATION: (21)..(21)
<223> OTHER INFORMATION: phosphate-dG

<400> SEQUENCE: 27
cggaattgcc aggacgaccg g                                              21

<210> SEQ ID NO 28
<211> LENGTH: 36
<212> TYPE: DNA
<213> ORGANISM: Artificial Sequence
<220> FEATURE:
<223> OTHER INFORMATION: Synthetic probe

<400> SEQUENCE: 28
cggtgtactc accgttccgc agaccactat ggctct                              36

<210> SEQ ID NO 29
<211> LENGTH: 31
<212> TYPE: DNA
<213> ORGANISM: Artificial Sequence
<220> FEATURE:
<223> OTHER INFORMATION: Synthetic probe
<220> FEATURE:
<221> NAME/KEY: modified_base
<222> LOCATION: (1)..(1)
<223> OTHER INFORMATION: 6-carboxy-fluorescein-dC
<220> FEATURE:
<221> NAME/KEY: modified_base
<222> LOCATION: (15)..(15)
<223> OTHER INFORMATION: BHQ-2-dT
<220> FEATURE:
<221> NAME/KEY: modified_base
<222> LOCATION: (31)..(31)
<223> OTHER INFORMATION: phosphate-dG

<400> SEQUENCE: 29
cggtgtactc accgttccgc agaccactat g                                   31

<210> SEQ ID NO 30
<211> LENGTH: 33
<212> TYPE: DNA
<213> ORGANISM: Artificial Sequence
<220> FEATURE:
<223> OTHER INFORMATION: Synthetic probe

<400> SEQUENCE: 30
gggcgtgccc ccgcaagact gctagccgag tag                                 33

<210> SEQ ID NO 31
<211> LENGTH: 30
<212> TYPE: DNA
<213> ORGANISM: Artificial Sequence
<220> FEATURE:
<223> OTHER INFORMATION: Synthetic probe

<400> SEQUENCE: 31
tggactcagt ccttggtcat ctcaccttct                                     30

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
ctcgcaagca ccctatcagg cagt                                           24
```

METHOD FOR PREVENTING HIGH MOLECULAR WEIGHT PRODUCTS DURING AMPLIFICATION

CROSS-REFERENCES TO RELATED APPLICATIONS

This application is a non-provisional of application Ser. No. 61/715,464, filed on Oct. 18, 2012, which claims the benefit of EP12189009.0 also filed on Oct. 18, 2012, the entire contents of which are hereby incorporated herein by reference in their entireties.

FIELD OF THE INVENTION

The present invention belonging to the field of in-vitro diagnostics relates to improved methods for amplifying and detecting a nucleic acid target that may be present in a biological sample comprising at least a primer pair for generating an amplicon, wherein at least one primer is modified at the 5' terminus with a polyN sequence being non-complementary to the target sequence, and a detectable probe specific for said amplicon. The improvement is in particular based on the fact that the formation of side products other than the designed amplicon, i.e. of high molecular weight products during amplification is prevented or partly or completely suppressed. If the present invention is used in diagnostic type of applications, false-negative or false-positive results are avoided. The invention further provides use of appropriately modified primers and a kit comprising said primers for preventing or suppressing the formation of high molecular weight products during amplification and detection of the nucleic acid target.

BACKGROUND OF THE INVENTION

In the field of molecular diagnostics, the amplification and detection of nucleic acids is of considerable significance. Examples for diagnostic applications of nucleic acid amplification and detection are the detection of viruses such as Human Papilloma Virus (HPV), West Nile Virus (WNV) or the routine screening of blood donations for the presence of Human Immunodeficiency Virus (HIV), Hepatitis-B (HBV) and/or -C Virus (HCV). Said amplification and detection techniques are also suitable for bacterial nucleic acid targets or the analysis of oncology markers or the like.

The most prominent and widely used method for amplification and detection of nucleic acid targets is the Polymerase Chain Reaction utilizing a polymerase enzyme (PCR, U.S. Pat. No. 4,683,195 and U.S. Pat. No. 4,683,202). Related significant improvements are, e.g., real-time detection of amplified products during PCR utilizing modified oligonucleotides carrying reporter groups or labels known as hydrolization or 5'-nuclease probes such as used in commercial assays on COBAS® TaqMan® (U.S. Pat. No. 5,210,015 and U.S. Pat. No. 5,487,972). Other improved amplification and detection methods are known as Molecular Beacons technology (WO 95/13399) or methods utilizing an oligonucleotide comprising a minor groove binder (MGB) portion (WO 03/062445 and WO 2006/135765).

It is further known that the use of primers containing an added oligonucleotide with a high GC content at the 5' terminus of at least one of these primers displays an improvement in amplification efficiency (Q. Liu et al., Genome Research vol. 7 (1997), p. 389-398; WO 01/94638; US 2004/0110182). The final quantity of the amplified product after approximately 12 to 40 cycles of PCR is markedly higher for primers to which e.g. a GGAC unit has been added to the 5' termini than for the unmodified primers.

Afonina et al. (BioTechniques vol. 43(3) (2007), p. 1-3; WO 2006/135765) describe the increase of real-time PCR fluorescent signal and thereby obtaining improved amplification efficiency by using primers with short adenine and thymine rich flaps, scattered randomly, at the 5' terminus and minor groove binder (MGB) fluorescent hybridization probes.

Furthermore, in some PCR assays, side products like the formation of high molecular weight products might have substantial impact on the amplification efficiency, e.g., creates false positive or false negative results. In particular for low titer samples a decrease or dropout of detection signals is expected due to the formation of high molecular weight amplification products leading to false negative results. The amplification efficiency is usually more reduced as more PCR cycles are carried out.

In quantitative PCR reactions often an internal validation and quantitation standard is added and is co-amplified. It controls the preparation and amplification processes and compensates for effects of inhibition. Formation of high molecular weight products during amplification of the internal standard may lead to suppressed signals and an invalid standard so that the PCR reaction which is controlled by the internal validation and quantitation standard is invalidated.

A source of false positive results is "carryover contamination", where a PCR product (amplicon) from a prior PCR reaction contaminates subsequent PCR assays. The contaminant may be transmitted by a technician, an instrument or even via aerosol. High molecular weight products are more resistant than single amplicons to contamination prevention measures like uracil-DNA glycosylases (U.S. Pat. No. 6,713,294) and therefore significantly increase the risk of carryover contamination. In a true negative sample, where the target nucleic acid is absent, the contaminant creates a false positive result. In a true positive sample, where the target nucleic acid is present, the contaminant is co-amplified with the true target. Such co-amplification may distort a result of a quantitative assay, where the exact amount of the true target must be determined.

Thus, there is a need in the art to provide a method for simple and reliable amplification and detection of a nucleic acid target. There is in particular a need to provide an appropriate improved method with focus on suppressing high molecular weight by-products.

DESCRIPTION OF THE INVENTION

The present invention relates to new methods and uses for amplifying and detecting a nucleic acid target that may be present in a biological sample comprising at least a primer pair for generating an amplicon, wherein at least one primer is modified at the 5' terminus with a polyN sequence being non-complementary to the target sequence, and a detectable probe specific for said amplicon or a DNA binding dye. The improvement is in particular based on the fact that the formation of high molecular weight products during amplification is prevented or partly or completely suppressed, and thus e.g. false-negative or false-positive results are therefore avoided. Thus, one subject of the invention is:

A method for amplifying and detecting a nucleic acid target in a biological sample, wherein the formation of high molecular weight products during amplification is prevented or suppressed, said method comprising the following steps:
a) Contacting the nucleic acids in said sample with amplification reagents comprising at least a polymerase, nucleoside triphosphates or other nucleoside monomers, an extended forward or an extended reverse primer for generating an amplicon and a detectable probe specific for said amplicon or a DNA binding dye, wherein at least one of said extended forward or said reverse primers comprises a polyN sequence added to the 5' terminus of the primer being non-complementary to the target sequence;
b) Incubating said nucleic acids with said amplification reagents for a period of time and under conditions sufficient for an amplification reaction to occur; and
c) Detecting said amplicon via said detectable probe or DNA binding dye.

The present invention further relates to new methods and uses for amplifying and detecting a nucleic acid target that may be present in a biological sample comprising at least a primer pair for generating an amplicon, wherein both primers are modified at the 5' terminus with a polyN sequence being non-complementary to the target sequence, and a detectable probe specific for said amplicon or a DNA binding dye. The improvement is in particular based on the fact that the formation of high molecular weight products during amplification is prevented or partly or completely suppressed, and thus e.g. false-negative or false-positive results are therefore avoided. Thus, one subject of the invention is:

A method for amplifying and detecting a nucleic acid target in a biological sample, wherein the formation of high molecular weight products during amplification is prevented or suppressed, said method comprising the following steps:
a) Contacting the nucleic acids in said sample with amplification reagents comprising at least a polymerase, nucleoside triphosphates or other nucleoside monomers, an extended forward and an extended reverse primer for generating an amplicon and a detectable probe specific for said amplicon or a DNA binding dye, wherein said extended forward and reverse primers comprise each a polyN sequence added to the 5' terminus of the primer being non-complementary to the target sequence;
b) Incubating said nucleic acids with said amplification reagents for a period of time and under conditions sufficient for an amplification reaction to occur; and
c) Detecting said amplicon via said detectable probe or DNA binding dye.

A further subject of the invention is:

A method for preventing or suppressing the formation of high molecular weight products during PCR amplification, said method comprising the following steps:
a) Contacting the nucleic acids in a biological sample with amplification reagents comprising at least a polymerase, nucleoside triphosphates or other nucleoside monomers, an extended forward and/or an extended reverse primer for generating an amplicon and a detectable probe specific for said amplicon or a DNA binding dye, wherein at least one of said extended forward and/or reverse primers comprises a polyN sequence added to the 5' terminus of the primer being non-complementary to the target sequence;
b) Incubating said nucleic acids with said amplification reagents for a period of time and under conditions sufficient for an amplification reaction to occur; and
c) Detecting said amplicon via said detectable probe or DNA binding dye.

The methods according to the invention add a number of improvements to the art: By preventing or suppressing the formation of high molecular weight products during PCR subsequent detection of the amplicon is more reliable as fluorescence suppression is avoided. This applies to amplification of both the target and/or of an internal standard. High molecular weight products, but not amplicons lead to fluorescence suppression in subsequent PCR reactions. The inventive methods are in particular of advantage for the detection of samples wherein the nucleic acid target is absent or only contained in a low titer amount when usually at least 20 PCR cycles are applied. In some of such embodiments the PCR cycles are terminated after more than 30, sometimes more than 40, more than 50 or in some embodiments more than 60 cycles. For most of these samples the amplification reaction is not terminated prior to 50 cycles. Suppression of such PCR reactions is even more pronounced under conditions of underlying low levels of contamination from previous PCR reactions.

The methods according to the invention to prevent or suppress the formation of high molecular weight products by use of extended primers may also be useful for amplification methods in which no probe or DNA binding dye is needed for detection.

The expression "polyN" according to the present invention refers to a polynucleotide sequence which may contain all five natural bases adenine (A), guanine (G), cytosine (C), thymine (T) and uracil (U) or only four, three, two or one of these natural bases. The polyN sequence according to the invention comprises at least two or multiple identical bases, e.g., (A)m, (T)m, (G)m, (C)m, (U)m, wherein m is a number of 2 to 10, or different bases, e.g., (AT)n, (AG)n, (AC)n, (TA)n, (UA)n, (GA)n or (CG)n, wherein n is a number of 1 to 5, and usually not more than 50 nucleotides in total. The polyN sequence may be added to at least one of the primers used. The polyN sequence added to two or more primers may be identical or different. In some embodiments of the invention, forward and reverse primers contain identical polyN sequences.

According to one embodiment, the invention provides the methods described above, wherein the polyN sequence described in step a) comprises a polyA, polyT, polyAT, polyU, polyC or polyG sequence. PolyN sequences which comprise 100% of one type of nucleotide or two different nucleotides, deriving from adenine (A), thymidine (T), adenine-thymidine (AT), uracil (U), cytosine (C) or guanine (G), and in total 2 to 10 nucleotides or 4 to 6 nucleotides in length are used according to the invention. PolyN sequence tails comprising four to six consecutive adenine (A) bases are in particular used according to the invention. The polyN tail may also contain modified nucleotides like alkylated nucleotides such as N4-ethyl-dC, N6-methyl-dA or 2'-O-methyl-nucleotides or the like, as long as the modified nucleotide has the capability of hybridizing to its complement and of serving as template in an amplification reaction.

Further, the invention provides a kit for amplifying and detecting a target nucleic acid in a biological sample by any of the methods described above. Said kit comprises at least one polymerase, e.g., a thermostable polymerase, at least four different nucleoside triphosphates or other nucleoside monomers, at least one extended forward and/or one extended reverse primer for generating at least one amplicon, wherein at least one of said extended forward and reverse primers comprises a polyN sequence added to the 5' terminus of the primer being non-complementary to the target sequence, and at least one detectable probe specific for said amplicon or a DNA binding dye. Kits according to the invention in particular are those, wherein said polyN sequence comprises a polyA, a polyT, a polyAT, a polyU, a polyC, a polyG sequence being 2 to 10 nucleotides in length. The polyN sequence may be attached to at least one of the primers used. The polyN sequence attached to two or more of the primers may be identical or different. In some embodiments of the invention, the kit comprises a forward primer and a reverse primer containing identical polyN sequences. The kit may further comprise additional primers and probes, enzymes like uracil-N-glycosylase, aptamer, buffer components and detergents or the like.

To aid in understanding of the invention, several terms are defined below.

A "biological sample" can be any sample of natural origin. A "biological sample" is for example derived from a human and is a body liquid or tissue of the body. In one embodiment of the invention, the "biological sample" is blood.

The term "nucleoside" refers to a compound consisting of a base linked to the C-1' carbon of a sugar, for example, ribose or deoxyribose. The base portion of the nucleoside is usually a heterocyclic base, e.g., a purine or pyrimidine.

The term "nucleotide" refers to a phosphate ester of a nucleoside, as a monomer unit or within a polynucleotide. "Nucleoside 5'-triphosphate" refers to a nucleotide with a triphosphate ester group attached to the sugar 5'-carbon position, and is sometimes denoted as "NTP", or "dNTP" and "ddNTP". A modified nucleotide is any nucleotide (e.g., ATP, TTP, UTP, GTP or CTP) that has been chemically modified, typically by modification of the base, sugar or phosphate moiety. Modified nucleotides include, for example but are not limited to, base moieties such as N4-ethylcytosine, N6-methyladenine, N6-tert-butylbenzyladenine or N4-tert-butylbenzylcytosine, 5-methylcytosine, 6-mercaptopurine, 5-fluorouracil, 5-iodouracil and 6-thioguanine or sugar modifications such as 2'-O-methyl-ribose and 2'-fluoro- or 2'-amino-2'-deoxyribose or the like. As used herein, the term "nucleotide analog" refers to any nucleotide that is non-naturally occurring.

The expression "other nucleoside monomer" refers to phosphate activated nucleosides other than standard nucleoside triphosphates which can be employed in enzymatical polynucleotide synthesis, as for example nucleoside tetraphosphates or the like.

The terms "target nucleic acid" and "target region" refers to a region of a nucleic acid which is to be amplified, detected, or otherwise analyzed. The sequence to which a primer or probe hybridizes can be referred to as a "target sequence".

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA, as well as a double strand of RNA and DNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90-99; the phosphodiester method of Brown et al., 1979, Meth. Enzymol. 68:109-151; the phosphoramidite method of Beaucage et al., 1981, Tetrahedron Lett. 22:1859-1862; and the solid support method described in U.S. Pat. No. 4,458,066. A review of synthesis methods is provided in Goodchild, 1990, Bioconjugate Chemistry 1(3):165-187.

The terms "amplification," "amplifying" and the like refer generally to any process that results in an increase in the copy number of a molecule or set of related molecules. As it applies to polynucleotide molecules, amplification means the production of multiple copies of a polynucleotide molecule, or a portion of a polynucleotide molecule, typically starting from a small amount of a polynucleotide (e.g., a viral genome), where the amplified material (amplicon, PCR amplicon) is typically detectable. Amplification of polynucleotides encompasses a variety of chemical and enzymatic processes. The generation of multiple DNA copies from one or a few copies of a template RNA or DNA molecule during a polymerase chain reaction (reverse transcription PCR, PCR), a strand displacement amplification (SDA) reaction, a transcription mediated amplification (TMA) reaction, a nucleic acid sequence-based amplification (NASBA) reaction, or a ligase chain reaction (LCR) are forms of amplification. Amplification is not limited to the strict duplication of the starting molecule. For example, the generation of multiple cDNA molecules from a limited amount of viral RNA in a sample using reverse transcription PCR is a form of amplification. Furthermore, the generation of multiple RNA molecules from a single DNA molecule during the process of transcription is also a form of amplification.

The term "amplicon" refers to a polynucleotide molecule (or collectively the plurality of molecules) produced following the amplification of a particular target nucleic acid. The amplification method used to generate the amplicon can be any suitable method, most typically, for example, by using a PCR methodology. An amplicon is typically, but not exclusively, a DNA amplicon. An amplicon can be single-stranded or double-stranded, or in a mixture thereof in any concentration ratio.

The term "high molecular weight products" refers to oligomers (or polymers or concatemers) of amplicons and thus containing multiple binding sites for primers, probes and DNA binding dyes. High molecular weight products are increasingly formed as more PCR cycles are carried out, in particular because the amplicons act non-specifically as primers.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 2nd Edition 1989, Part 1-3, Molecular Cloning—A Laboratory Manual, Cold Spring Harbor Laboratory, Cold Spring Harbor, N.Y.).

Generally, stringent conditions are selected to be about 5° C. lower than the thermal melting point (Tm) for the specific sequence at a defined ionic strength and pH value. The Tm is the temperature (under defined ionic strength and pH) at which 50% of the duplexes have dissociated. Relaxing the stringency of the hybridisation conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of RNA or DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is for example a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template nucleic acid, but must be sufficiently complementary to hybridize with the template. Primers can incorporate additional features which increase the specificity of binding to the target sequence (such as a modified nucleotide like the 3' terminal alkylated nucleotides described in EP 0 866 071 and in EP 1 201 768) or allow for the detection or immobilization of the primer but do not alter the basic property of the primer, that of acting as a point of initiation of RNA or DNA synthesis. For example, primers may contain an additional nucleic acid sequence at the 5' end which does not hybridize to the target nucleic acid, but which facilitates cloning of the amplified product and/or according to the invention suppression or prevention of the formation of high molecular weight products. The region of the primer which is sufficiently complementary to the template to hybridize is referred to herein as the hybridizing region.

The term "extended primer" or "polyN extended primer" as used in this invention refers to a primer containing an additional polynucleotide sequence (polyN) at the 5' end which may contain all five natural bases adenine (A), guanine (G), cytosine (C), uracil (U) and thymine (T) or only four, three, two or one of these natural bases. In particular, the polyN sequence comprises at least two or multiple identical bases, e.g., (A)m, (T)m, (G)m, (C)m or (U)m, wherein m is a number of 2 to 10, or different bases, e.g., (AT)n, (AG)n, (AC)n, (TA)n, (UA)n, (GA)n or (CG)n, wherein n is a number of 1 to 5, respectively, and usually not more than 50 nucleotides in total. The polyN sequence may for example comprise a polyA, polyT, polyAT, polyU, polyC or polyG sequence. PolyN sequences which comprise 100% of one type of nucleotide or two different nucleotides, deriving from adenine (A), thymidine (T), adenine-thymidine (AT), uracil (U), cytosine (C) or guanine (G), and in total 2 to 10 nucleotides, 4 to 6 nucleotides in length are applied in most cases according to the invention. According to the invention at least one appropriately extended primer is used. The polyN sequence added to each of at least two extended primers may be identical or different.

The expression "polyN" according to the present invention refers to a polynucleotide sequence which may contain all five natural bases adenine (A), guanine (G), cytosine (C), uracil (U) and thymine (T) or only four, three, two or one of these natural bases. The polyN sequence comprises at least two or multiple identical bases, e.g., (A)m, (T)m, (G)m, (U)m, (C)m, wherein m is a number of 2 to 10, or different bases, e.g., (AT)n, (AG)n, (AC)n, (TA)n, (UA)n, (GA)n, or (CG)n, wherein n is a number of 1 to 5, and usually not more than 50 nucleotides in total. The polyN sequence added to two or more primers used may be identical or different. In a particular embodiment of the invention, forward and reverse primers contain polyN sequences, said polyN sequences might be identical or different. The polyN tail may also contain modified nucleotides like alkylated nucleotides such as N4-ethyl-dC, N6-methyl-dA or 2'-O-methyl-nucleotides or the like, as long as the modified nucleotide has the capability of hybridizing to its complement and of serving as template in an amplification reaction. In some embodiments it may be useful that only one primer, either forward or reverse primer, comprises a polyN tail.

In one embodiment, the invention provides the methods described above, wherein the polyN sequence described in step a) comprises a polyA, polyT, polyAT, polyU, polyC or polyG sequence. PolyN sequences which comprise 100% of one type of nucleotide or two different nucleotides, deriving from adenine (A), thymidine (T), adenine-thymidine (AT), uracil (U), cytosine (C) or guanine (G), and in total 2 to 10 nucleotides in length. PolyN sequences comprising 4 to 6 nucleotides in length are also used according to the invention. Sequence tails comprising four to six consecutive adenine (A) bases are in particular used according to the invention.

As used herein, the "upstream" primer refers to the primer whose extension product is a subsequence of the coding strand. The "downstream" primer refers to the primer whose extension product is a subsequence of the complementary non-coding strand.

As used herein, the "forward" primer refers to a primer extending in PCR from the start codon at the 3' end of the anti-sense strand towards the stop codon at the 5' end of the template DNA (nucleic acid target), while the "reverse" primer refers to a primer extending from the stop codon at the 5' end of the sense strand towards the start codon at the 3' end of the template DNA. The forward primer is usually designed to anneal to the template DNA upstream of the start codon, whereas the reverse primer is designed to anneal to a region of the template DNA downstream of the stop codon.

The term "probe", as used herein, refers to an oligonucleotide which forms a duplex structure with a sequence of a target nucleic acid due to complementary base pairing. Probes are used for detection or capture of the target nucleic acid. A probe is for example a single-stranded oligodeoxyribonucleotide. The probe typically will consist of, or contain, a "hybridizing region" consisting of for example 10 to 50 nucleotides, further for example 15 to 35 nucleotides, corresponding to a region of the target sequence.

"Corresponding" means at least substantially complementary to either the designated nucleic acid or its complement. A probe need not reflect the exact sequence of the target nucleic acid, but must be sufficiently complementary to hybridize with the target under the hybridization conditions chosen. A probe oligonucleotide can contain, or be bound to, additional features which allow for the detection or immobilization of the probe but do not significantly alter the hybridization characteristics of the hybridizing region. For example, probes may be labeled by the incorporation of one or more labeled nucleotides or by being bound to one or more separate detectable moieties. The labeled nucleotides or detectable moieties comprise for example, but are not limited to, fluorescent dyes like fluorescein, rhodamine, coumarin and cyanine or quencher dyes like Black Hole Quenchers such as BHQ-2 from Biosearch Technologies Inc., Novato, Calif. The probe may be for instance a hydrolization or 5'-nuclease probe, a molecular beacon probe, a minor groove binder containing probe or a hybridization probe and the like as known to the skilled artisan.

As used herein, an oligonucleotide primer or probe is "specific" for a target sequence if the number of mismatches present between the oligonucleotide and the target sequence is less than the number of mismatches present between the oligonucleotide and non-target sequences. Hybridization conditions can be chosen under which stable duplexes are formed only if the number of mismatches present is no more than the number of mismatches present between the oligonucleotide and the non-target sequence. Under such conditions, the target-specific oligonucleotide can form a stable duplex only with a target sequence. Thus, the use of target-specific probes under suitably stringent hybridization conditions enables the detection of a specific target sequence. Similarly, the use of target-specific primers under suitably stringent amplification conditions enables the specific amplification of those target sequences which contain the target primer binding sites.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The term "thermostable" as applied to an enzyme, in particular refers to an enzyme that retains its biological activity at elevated temperatures (e.g., at 55° C. or higher), or retains its biological activity following repeated cycles of heating and cooling. The polymerase enzyme initiates synthesis at the 3' end of the primer and proceeds in the direction toward the 5' end of the template until synthesis terminates. A purified thermostable polymerase enzyme is described more fully, e.g., in U.S. Pat. No. 4,889,818, and is commercially available, e.g., from Roche Diagnostics GmbH/Germany.

The term "the complement of" a given nucleic acid refers specifically to the antiparallel polynucleotide strand, that means to the nucleic acid which has both the same length as, and is exactly complementary to, the given nucleic acid. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands (no mismatches in the polynucleotide duplex). However, complementarity need not be perfect; stable duplexes, for example, may contain mismatched base pairs or unmatched bases. The terms "partial complementarity," "partially complementary," "incomplete complementarity" or "incompletely complementary" and the like refer to any alignment of bases between antiparallel polynucleotide strands that is less than 100% perfect (e.g., there exists at least one mismatch or unmatched base in the polynucleotide duplex). Thus, the complement of a nucleic acid refers to a single, uniquely defined sequence.

The terms "detectable", "label" or "reporter," in their broadest sense, refer to any moiety or property that is detectable, or allows the detection of that which is associated with it. For example, a polynucleotide that comprises a label is detectable (and in some aspects is referred to as a probe). Ideally, a labeled polynucleotide permits the detection of a hybridization complex that comprises the polynucleotide. In some aspects, e.g., a label is attached (covalently or non-covalently) to a polynucleotide. In various aspects, a label can, alternatively or in combination: (i) provide a detectable signal; (ii) interact with a second label to modify the detectable signal provided by the second label, e.g., FRET; (iii) stabilize hybridization, e.g., duplex formation; (iv) confer a capture function, e.g., hydrophobic affinity, antibody/antigen, ionic complexation, or (v) change a physical property, such as electrophoretic mobility, hydrophobicity, hydrophilicity, solubility, or chromatographic behavior. Labels vary widely in their structures and their mechanisms of action.

Examples of labels include, but are not limited to, fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), Texas Red is commercially available from, e.g., Life Technologies (Molecular Probes, Inc.) (Grand Island, N.Y.). Dyes of the cyanine family include, e.g., CY2, CY3, CY5, CY5.5 and CY7, and are commercially available from, e.g., GE Healthcare Life Sciences (Piscataway, N.J., USA).

The term "DNA binding dye" or "DNA intercalating dye" refers to dye molecules which are capable of binding to double stranded nucleic acids and emit a fluorescence signal upon binding, such as SYBRGREEN I and SYBRGOLD available from Life Technologies (Grand Island, N.Y.) or Lightcycler 480 Resolight from Roche Diagnostics (Germany).

The term "FRET" (fluorescence resonance energy transfer) and equivalent terms refer generally to a dynamic distance-dependent interaction between electron states of two dye molecules in which energy is transferred from a donor molecule to an acceptor molecule without emission of a photon from the donor molecule. The efficiency of FRET is dependent on the inverse of the intermolecular separation between the dyes, making it useful over distances comparable with the dimensions of biological macromolecules. Generally, FRET allows the imaging, kinetic analysis and/or quantitation of co-localizing molecules or conformational changes in a single molecule with spatial resolution beyond the limits of conventional optical microscopy. In general, FRET requires, (a) the donor and acceptor molecules must be in close proximity (typically, e.g., 10-100 Å), (b) the absorption spectrum of the acceptor must overlap the fluorescence emission spectrum of the donor, and (c) the donor and acceptor transition dipole orientations must be approximately parallel.

In most FRET applications, the donor and acceptor dyes are different, in which case FRET can be detected by the appearance of sensitized fluorescence of the acceptor or by quenching of donor fluorescence. In some cases, the donor and acceptor are the same, and FRET can be detected by the resulting fluorescence depolarization. Use of a single donor/acceptor molecule in a FRET system is described, for example, in U.S. Pat. No. 7,312,302, by Packard and Komoriya.

FRET has become an important technique for investigating a variety of biological phenomena that are characterized by changes in molecular proximity. FRET techniques are now pervasive in many biological laboratories, and have been adapted for use in a variety of biological systems, including but not limited to, detection of nucleic acid hybridization, real-time PCR assays and SNP detection, structure and conformation of proteins, spatial distribution and assembly of protein complexes, receptor/ligand interactions, immunoassays, probing interactions of single molecules, structure and conformation of nucleic acids, primer-extension assays for detecting mutations, automated DNA sequencing, distribution and transport of lipids, membrane fusion assays (lipid-mixing assays of membrane fusion), membrane potential sensing, fluorogenic protease substrates, and indicators for cyclic AMP and zinc.

The term "hydrolization probe" or "5'-nuclease probe" denotes probes used for most applications according to the present invention and used in PCR reactions i.e. on the COBAS® TaqMan® systems. Such hydrolization or 5'-nuclease probes consist of a single-stranded hybridization probe which is normally labeled with two fluorescent moieties. When a first fluorescent moiety is excited with light of a suitable wavelength, the absorbed energy is transferred to a second fluorescent moiety according to the principle of Fluorescence Resonance Energy Transfer (FRET). The second fluorescence moiety is generally a quencher molecule which may also be a non-fluorescent quencher like BHQ-2. Typical fluorescent dyes used in this format are for example, among others, FAM, HEX, CY5, JA270, Cyan 500 and CY5.5. During the annealing step of the PCR reaction, the labeled hybridization probe binds to the target nucleic acid (i.e., the amplification product) and is degraded by the 5' to 3' exonuclease activity of the Taq DNA polymerase or another suitable polymerase as known by the skilled artisan, such as ZO5 polymerase, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescence moiety can be detected. In both detection formats, the LightCycler® and the TaqMan® technology, the intensity of the emitted signal can be correlated with the number of original target nucleic acid molecules.

The expression "hepatitis C virus type" refers to the categorization of a hepatitis C virus (HCV) based on its genomic organization (e.g., phylogenetic analysis). The categorization of an HCV isolate into a particular type category reflects its genomic relatedness to other HCV isolates and its relatively lesser relatedness to other HCV isolates. The HCV typing nomenclature used herein is consistent with the widely adopted nomenclature revised and proposed by Simmonds et al (2005) "Consensus Proposals for a Unified System of Nomenclature of Hepatitis C Virus Genotypes", Hepatology 42, No. 4: 962-973. The system of Simmonds et al (2005) places the known HCV isolates into one of six (6) HCV genotypes, namely genotypes 1 through 6. Each genotype is further subdivided into groupings termed subtypes that reflect relatedness among strains of the same genotype. An HCV subtype is written by a lowercase roman letter following the genotype, e.g., subtype 1a, subtype 1c, subtype 6a, etc. Genetic variants found within an individual isolate are termed quasi species. Approximately 100 HCV subtypes encompassing all 6 genotypes are known worldwide; the number of subtypes is not static; as more HCV isolates are studied and sequenced, it is likely that additional subtypes (and possibly genotypes) may be recognized.

The term "virus types" can refer to either genotypes or subtypes. It is noted that as used herein, the term "HCV type" can mean HCV genotype or HCV subtype. The term "HCV typing" means assigning the experimental (e.g., unknown type) HCV to a known genotype (e.g., 1, 2, 3, 4, 5 or 6, or a subset thereof) or assigning the experimental HCV to a known subtype (e.g., 1a, 1b, 1c, 2a, 2b, 2c, etc., or a subset thereof). In contrast, it is also noted that as commonly used in the art, the term "HCV genotyping" most frequently refers to assigning an HCV to one of any subtype of HCV, e.g., most typically, 1a, 1b, 1c, 2a, 2b, 2c, etc. However, as used herein, the term "genotyping" refers to assignment only to 1, 2, 3, 4, 5 or 6.

The term "kit" is used in reference to a combination of articles that facilitate a process, method, assay, analysis or manipulation of a sample. Kits can contain written instructions describing how to use the kit (e.g., instructions describing the methods of the present invention), chemical reagents or enzymes required for the method, primers and probes, as well as any other components. In some embodiments, the present invention provides kits for "closed-tube" detection employing Real-Time (RT)-PCR. These kits can include, for example, but are not limited to, reagents for sample collection (e.g., the collection of a blood sample), reagents for the collection and purification of RNA and/or DNA, for example, from blood, reagents for amplification and detection including optionally a reverse transcriptase enzyme activity, primers suitable for reverse transcription and first strand and second strand cDNA synthesis to produce one or more amplicons but at least one forward and/or one reverse extended primer, uracil-DNA glycosylase, a thermostable DNA-dependent DNA polymerase and (deoxyribo)nucleoside triphosphates. In some embodiments, the enzyme comprising reverse transcriptase activity and thermostable DNA-dependent DNA polymerase activity are the same enzyme, e.g., *Thermus* sp. ZO5 polymerase or *Thermus thermophilus* polymerase.

Conventional techniques of molecular biology and nucleic acid chemistry, which are within the skill of the art, are fully explained in the literature, see, for example, Sambrook et al., 2nd Edition 1989, Part 1-3, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); and a series, Methods in Enzymology (Academic Press, Inc.).

In principle, all kinds of nucleic acid targets can be amplified and detected with the inventive methods. The methods are, however, in particular applied to test high target containing samples or controls wherein high molecular weight products are generated in PCR reactions by polymerization of amplicons formed in earlier PCR cycles. Examples for high target nucleic acids according to the invention are nucleic acids of viruses such as, e.g., Human Papilloma Virus (HPV), West Nile Virus (WNV) or those used for the routine screening of blood donations for the presence of Human Immunodeficiency Virus (HIV), Hepatitis-B (HBV) and/or Hepatitis-C(HCV). The inventive methods are, however, also suitable for bacterial targets or the analysis of oncology markers or the like.

In particular, Hepatitis-C Virus (HCV) infection is a growing worldwide concern. HCV infections are often persistent and induce chronic liver disease, manifested in cirrhosis of the liver and hepatocellular carcinoma. HCV is the leading cause for liver transplantation in the United States. Worldwide, approximately one million new HCV infections are reported annually; in the United States alone, an estimated four million persons are infected and 30,000 new infections occur annually.

Currently, HCV is responsible for an estimated 8,000 to 10,000 deaths annually in the United States. Without the development of improved diagnostics and therapeutics, that number is expected to dramatically increase world-wide within the next years.

The HCV genome is highly polymorphic, and a number of strains (termed genotypes and subtypes) have been characterized. The different viral types correlate with different disease outcomes and different responsiveness to therapeutic regimens.

The HCV genomic structure/organization is most similar to that of the family Flaviviridae. Consistent with the known functions of most flavivirus proteins, the N-terminal HCV proteins are likely structural (including the C (capsid/core), E1 and E2 envelope proteins) and the C-terminal non-structural proteins, including NS2 (metalloprotease), NS3 (serine-protease/helicase), NS4 and NS5 (NS5B RNA polymerase) are believed to function in viral replication.

Following identification and characterization of the prototypical HCV isolate (now termed HCV 1a), other isolates from around the world were (and continue to be) identified. Sequence comparisons reveal that these unique isolates can differ from each other by as much as 35% nucleotide non-identity over the full length of the HCV genome (Okamoto et al. (1992) Virology 188:331-341). Sequence variability is observed throughout the viral genome, with some regions showing more variability than others. For example, generally high sequence conservation is observed in the 5'-UTR region; conversely, some regions, including the envelope (E) region, show hypervariable nucleotide sequences.

Knowing the viral genotype (and/or subtype) present in an infection provides the clinician with an important indicator for determining an optimal course of treatment for an infected patient. However, the development of simple, diagnostic methods that can differentiate the ever-increasing number of known HCV types has become a challenge.

The inventive methods for amplifying and detecting a target nucleic acid, wherein the target nucleic acid is a viral nucleic acid, for example HCV, are embodiments according to the invention.

The present invention thus provides improved oligonucleotide primers (extended primers) which enable the polymerase chain reaction (PCR) amplification of a region of high sequence conservation, e.g., the 5' UTR region, present in the genome of most of the HCV types known to date. The present invention also provides improved oligonucleotide probes which enable the detection of HCV nucleic acid by hybridization.

An important advantage of the primers of the present invention is that they enable amplification of all HCV types, without the simultaneous amplification of non-target sequences. Thus, the primers enable an HCV detection assay capable of detecting all types of HCV from samples originating from all regions of the world.

Thus, one object of the present invention is a method for amplifying and detecting a nucleic acid target, e.g., a nucleic acid of HCV, in a biological sample, wherein the formation of high molecular weight products during amplification is prevented or suppressed, said method comprising the following steps:

a) Contacting the nucleic acids in said sample with amplification reagents comprising at least a polymerase, nucleoside triphosphates or other nucleoside monomers, an extended forward and/or an extended reverse primer for generating an amplicon and a detectable probe specific for said amplicon or a DNA binding dye, wherein said extended forward primer is a first HCV specific oligonucleotide and said reverse primer is a second HCV specific oligonucleotide, at least one of said primers comprising a polyN sequence added to the 5' terminus of the primer and being non-complementary to the target sequence;

b) Incubating said nucleic acids with said amplification reagents for a period of time and under conditions sufficient for an amplification reaction to occur; and c) Detecting said amplicon via said detectable probe or DNA binding dye.

In a particular embodiment of the invention the method comprises primers comprising a polyN sequence at the 5' end, said polyN sequence comprising a polyA, polyT, polyAT, polyU, polyC or polyG sequence. PolyN sequences which comprise 100% of one defined selected nucleotide or two defined selected nucleotides like adenine (A), thymidine (T), adenine-thymidine (AT), uracil (U), cytosine (C) or guanine (G) and in total 2 to 10 nucleotides. PolyN sequences comprising 4 to 6 nucleotides in length are in particular applied according to the invention. PolyN sequences comprising 4 to 6 consecutive adenine (A) nucleotides are most particular used according to the invention.

HCV specific primers according to the invention are, e.g., oligonucleotides like polyN containing primers of sequence GCAGAAAGCGTCTAGCCATGGCGTTA (SEQ ID NO: 1) used as forward primer and GCAAGCACCCTATCAGGCAGTACCACAA (SEQ ID NO: 2) used as reverse primer. Primers which are further modified at the 3' terminal nucleotide, e.g., alkylated at the exocyclic amino group of adenosine, may also be used according to the invention.

Another object of the present invention is a method for preventing or suppressing the formation of high molecular weight products during PCR amplification, said method comprises the following steps:

a) Contacting the nucleic acids in a biological sample with amplification reagents comprising at least a polymerase, nucleoside triphosphates or other nucleoside monomers, an extended forward and/or an extended reverse primer for generating an amplicon and a detectable probe specific for said amplicon or a DNA binding dye, wherein said extended forward primer and said reverse primer are both specific for the nucleic acid target to be determined, e.g., HCV, at least one of said primers comprising a polyN sequence added to the 5' terminus of the primer and being non-complementary to the target sequence;

b) Incubating said nucleic acids with said amplification reagents for a period of time and under conditions sufficient for an amplification reaction to occur; and c) Detecting said amplicon via said detectable probe or DNA binding dye.

In one embodiment of the invention the method comprises primers comprising a polyN sequence at the 5' end, said polyN sequence comprising a polyA, polyT, polyAT, polyU, polyC or polyG sequence. PolyN sequences which comprise 100% of one defined selected nucleotide or two defined selected nucleotides like adenine (A), thymidine (T), adenine-thymidine (AT), uracil (U), cytosine (C) or guanine (G) and in total 2 to 10 nucleotides in length are used according to the invention. Appropriate polyN sequences comprising 4 to 6 nucleotides in length are in particular applied according to the invention. PolyN sequences comprising four to six consecutive adenine (A) nucleotides are most particular used according to the invention.

HCV specific primers according to the invention are, e.g., oligonucleotides like polyN containing primers of sequence GCAGAAAGCGTCTAGCCATGGCGTTA (SEQ ID NO: 1) used as forward primer and GCAAGCACCCTATCAG-GCAGTACCACAA (SEQ ID NO: 2) used as reverse primer.

In particular, according to the present invention a pair of oligonucleotide primers is used for amplification of HCV nucleic acid, wherein said primer pair is selected from the group consisting of

```
                                        (SEQ ID NO: 3)
AAAAGCAGAAAGCGTCTAGCCATGGCGTTA
and
                                        (SEQ ID NO: 4)
AAAAGCAAGCACCCTATCAGGCAGTACCACAA, (SEQ ID NO: 5)
AAAAAAGCAGAAAGCGTCTAGCCATGGCGTTA
and
                                        (SEQ ID NO: 6)
AAAAAAGCAAGCACCCTATCAGGCAGTACCACAA, (SEQ ID NO: 7)
AAAAAAAAGCAGAAAGCGTCTAGCCATGGCGTTA
and
                                        (SEQ ID NO: 8)
AAAAAAAAGCAAGCACCCTATCAGGCAGTACCACAA, (SEQ ID NO: 9)
TTTTGCAGAAAGCGTCTAGCCATGGCGTTA
and
                                        (SEQ ID NO: 10)
TTTTGCAAGCACCCTATCAGGCAGTACCACAA, (SEQ ID NO: 11)
TTTTTTGCAGAAAGCGTCTAGCCATGGCGTTA
and
                                        (SEQ ID NO: 12)
TTTTTTGCAAGCACCCTATCAGGCAGTACCACAA, (SEQ ID NO: 13)
GGGCAGAAAGCGTCTAGCCATGGCGTTA
and
                                        (SEQ ID NO: 14)
GGGCAAGCACCCTATCAGGCAGTACCACAA (SEQ ID NO: 15)
ATATGCAGAAAGCGTCTAGCCATGGCGTTA
and
                                        (SEQ ID NO: 16)
ATATGCAAGCACCCTATCAGGCAGTACCACAA, (SEQ ID NO: 19)
AAAAAACCCACTCTATGTCCGGTC
and
                                        (SEQ ID NO: 20)
AAATGGCGTCTCCCACGCGGCTGG, (SEQ ID NO: 21)
ATATATGTACGCCGGAATTGCCGGAAA
and
                                        (SEQ ID NO: 22)
ATATATCTTTCCCCAGGACCTGCCGGT,
``` and any combination of any of said forward primers (SEQ ID NOS: 1, 3, 5, 7, 9, 11, 13, 15, 19 or 21) with any of the reverse primers (SEQ ID NOS: 2, 4, 6, 8, 10, 12, 14, 16, 20 or 22). According to one embodiment of the invention one or more additional primers may be added to the pair of primers to be used for HCV amplification, in particular a second target specific reverse primer, e.g., of sequence CTCGCAAGCACCCTATCAGGCAGT (SEQ ID NO: 32).

In particular, a pair of primers consisting at least of primer SEQ ID NO: 1 and primer SEQ ID NO: 2, primer SEQ ID NO: 3 and primer SEQ ID NO: 4, primer SEQ ID NO: 5 and primer SEQ ID NO: 6, SEQ ID NO: 9 and SEQ ID NO: 10 or primer SEQ ID NO: 15 and primer SEQ ID NO: 16 is used according to the invention. Furthermore, in particular, a set of primers consisting of primer SEQ ID NO: 1 with primers SEQ ID NO: 2 and SEQ ID NO: 32, of primer SEQ ID NO: 3 with primers SEQ ID NO: 4 and SEQ ID NO: 32, of primer SEQ ID NO: 5 with primers SEQ ID NO: 6 and SEQ ID NO: 32, of primer SEQ ID NO: 9 with primer SEQ ID NO: 10 and SEQ ID NO: 32, or of primer SEQ ID NO: 15 with primers SEQ ID NO: 16 and SEQ ID NO: 32, is used according to the invention. Another pair of 5'-polyN extended primers used according to the invention comprises polyN containing primers of sequences AAACCCACTCTATGTCCGGTC (SEQ ID NO: 23) and TGGCGTCTCCCACGCGGCTGG (SEQ ID NO: 24). Still another pair of 5'-polyN extended primers used according to the invention comprises polyN containing primers of sequence GTACGCCGGAATTGCCGGAAA (SEQ ID NO: 25) and CTTTCCCCAGGACCTGCCGGT (SEQ ID NO: 26). The primer pairs according to the invention may comprise at least one additional primer, in particular a second target specific reverse primer. The primers may contain modified nucleotides at the 3'-terminal region such as alkylated nucleotides like N4-ethyl-dC, N6-methyl-dA, N4-t-butylbenzyl-dC and N6-tert-butylbenzyl-dA as well as 2'-O-methyl-dU or the like.

The oligonucleotide probes of the present invention hybridize to regions of the HCV genome contained within the regions amplified using the primers of the present invention. The probes enable the specific detection of HCV nucleic acid from all types under a single set of hybridization conditions. When used to detect HCV nucleic acid amplified with the primers of the invention, the specificity of the probes further increases the specificity of HCV detection, thereby minimizing the probability of a false positive.

In one embodiment the present invention provides an oligonucleotide probe for the detection of HCV nucleic acid, wherein said oligonucleotide probe comprises a HCV specific nucleic acid sequence, a detectable label, e.g., a fluorescent moiety, and optionally a quencher moiety. A probe according to the present invention might, e.g., consist of a subsequence of FCGGAATTGCCAGGACGACCGGP (SEQ ID NO: 27) or a complement thereof, wherein F is a fluorescent dye as for example a 6-carboxy-fluorescein and P is a 3' terminal phosphate group, or a subsequence of CGGTGTACTCACCGTTCCGCAGACCACTATG-GCTCT (SEQ ID NO: 28) or the complement thereof, comprising a fluorescent dye of the cyanine family as for example CY5 attached to the 5' end and a 3' terminal phosphate group, or a subsequence of FCGGTGTACTCAC-CGQTTCCGCAGACC ACTATGP (SEQ ID NO: 29) or the complement thereof, wherein F is a fluorescent dye as for example a 6-carboxy-fluorescein, Q is a non-fluorescent quencher like BHQ-2 and P is a 3' terminal phosphate group, or a subsequence of GGGCGTGCCCCCGCAAGACT-GCTAGCCGAGTAG (SEQ ID NO: 30) or the complement thereof, comprising at least a fluorescent dye as for example CY5 and/or fluorescein, e.g., FAM, and a 3' terminal phosphate group. In a particular embodiment of the invention the probe is selected from the group consisting of GGGCGT-GCCCCCGCAAGACTGCTAGCCGAGTAG (SEQ ID NO: 30), comprising at least a fluorescent dye as for example CY5 and/or fluorescein, e.g., FAM, and a 3' terminal phosphate group, CGGTGTACTCACCGTTCCGCAGACCACTATGGCTCT (SEQ ID NO: 28) or a complement thereof, comprising at least a fluorescent dye as for example CY5 and/or fluorescein, e.g., FAM, and a 3' terminal phosphate group, FCGGAATTGCCAGGACGACCGGP (SEQ ID NO: 27), wherein F is 6-carboxy-fluorescein and P is a 3' terminal phosphate group, FCGGTGTACTCACCGQTTCCGCAGACCACTATGP (SEQ ID NO: 29), wherein F is 6-carboxy-fluorescein, Q is BHQ-2 and P is a 3' terminal phosphate group and a respective complement of these probe sequences.

All probe sequences according to the invention may be labeled with alternative dyes known to the skilled artisan and may be labeled at different positions of the oligonucleotide probes.

Another aspect of the invention relates to methods for amplifying a region of the gene from all known HCV types which comprise carrying out a PCR using at least an extended forward and/or extended reverse primer(s) of the invention, and detecting the amplified DNA using the probes of the invention or the respective complements of the probes. The primers and probes of the present invention or the respective complements of the probes enable particularly simple and rapid methods for the specific detection of HCV nucleic acid.

Another aspect of the invention relates to kits for amplifying and detecting a HCV nucleic acid which contain at least two HCV specific extended amplification primers of the invention. These kits can include additional reagents, such as the probes of the invention. The kits can also include one or more amplification reagents, e.g., polymerase, uracil-DNA glycosylases, aptamer, buffer salts, detergents, nucleoside triphosphates and other components like for example glycerin and/or DMSO.

The nucleic acid technique usually applied for the methods according to the invention is the polymerase chain reaction (PCR), a method for amplifying specific sequences of nucleic acids, making possible the rapid detection of nucleic acids present in a sample in what was previously an undetectably low quantity (see U.S. Pat. Nos. 4,683,195; 4,683,202 and 4,965,188). An exemplary method of detecting amplified nucleic acid is by hybridization with a sequence-specific oligonucleotide probe (see Saiki et al, 1986, Nature 324:163-166).

The detection methods may include, but are not limited to the binding or intercalating of specific dyes as ethidium bromide, SYBRGREEN or Lightcycler 480 Resolight which intercalate into the double-stranded DNA and change their fluorescence thereafter. In particular, the detecting step is performed in real time. By using commercially available real-time PCR instrumentation (e.g., LightCycler® or COBAS® TaqMan®), PCR amplification and detection of the amplification product can be combined in a single closed cuvette with dramatically reduced cycling time (e.g., EP 0 912 760, EP 1 033 411; EP 0 543 942, EP 0 919 565). Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory. As an alternative to real-time PCR as used in the LightCycler® technology (e.g., EP 0 912 760, EP 1 033 411), hydrolization or 5'-nuclease probe technology is for example applied according to the present invention. This technology as realized using the COBAS® TaqMan® utilizes a single-stranded hybridization probe labeled with two fluorescent moieties. When a first fluorescent moiety is excited with light of a suitable wavelength, the absorbed energy is transferred to a second fluorescent moiety according to the principle of Fluorescence Resonance Energy Transfer (FRET). The second fluorescence moiety is generally a quencher molecule which may also be a non-fluorescent quencher like BHQ-2. Typical fluorescent dyes used in this format are for example, among others, FAM, HEX, CY5, JA270, Cyan 500 and CY5.5. During the annealing step of the PCR reaction, the labeled hybridization probe binds to the target nucleic acid (i.e., the amplification product) and is degraded by the 5' to 3' exonuclease activity of the Taq DNA polymerase or another suitable polymerase as known by the skilled artisan, such as ZO5 polymerase, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescence moiety can be detected. In both detection formats, using the LightCycler® and the COBAS® TaqMan® analyzers, the intensity of the emitted signal can be correlated with the number of original target nucleic acid molecules. Hydrolization or 5'-nuclease probes are in particular used according to the invention.

As an alternative to FRET, an amplification product can be detected using a double-stranded DNA binding dye such as a fluorescent DNA binding dye (e.g., SYBRGREEN I® or SYBRGOLD®, available from Life Technologies (Molecular Probes) or Lightcycler 480 Resolight, available from Roche Diagnostics GmbH, Germany). Upon interaction with the double-stranded nucleic acid, such fluorescent DNA binding dyes emit a fluorescent signal after excitation with light at a suitable wavelength. A double-stranded DNA binding dye such as a nucleic acid intercalating dye also can be used (as described above). When double-stranded DNA binding dyes are used, a melting curve is usually performed for confirmation of the presence of the amplification product.

In another embodiment of the invention carryover contamination of amplification products such as amplicons and high molecular weight products (polymerized amplicon) originating from earlier PCR reactions are prevented. A popular and effective way of preventing carryover contamination involves the use of uracil-DNA glycosylases, abbreviated as "UDG" or "UNG" (EC 3.2.2.3). These enzymes comprising uracil-DNA glycosylase activity recognize uracil present in single-stranded or double-stranded DNA and cleave the N-glycosidic bond between the uracil base and the deoxyribose leaving an abasic site, see e.g. U.S. Pat. No. 6,713,294. These enzymes degrade well uracil containing amplicons of small size but less efficiently uracil containing large size high molecular weight products (polymerized amplicon). Thus, upon contamination, high molecular weight products may serve as target in subsequent PCR reactions potentially leading to false positive test results in a negative sample or incorrect titer in a positive sample. Furthermore, contamination and incomplete degradation by uracil-DNA glycosylases may lead to signal suppression in subsequent PCR reactions and thus false negative results or invalid test results as the polymerized amplicons with their manifold primer and probe binding sequences drain the reaction mix of primer and probes. Therefore prevention of high molecular weight products in PCR is crucial for obtaining correct test results in target negative and positive samples.

Nevertheless, the inventive method for amplifying and detecting a target nucleic acid in a biological sample is in particular performed in the presence of a uracil-DNA glycosylase. In the presence of uracil-DNA glycosylase, prevention or suppression by contaminating high molecular weight products from previous PCR reactions during amplification is further improved. Particularly suitable according to the present invention is the use of an uracil-DNA glycosylase in combination with at least one primer comprising a polyN tail that contains multiple adenine (A) and/or thymine (T) nucleotides.

Preparation of uracil-N-DNA glycosylase (UNG) optimized for the control of carryover contamination in amplification reactions has been disclosed for example, in U.S. Pat. No. 6,187,575. The use of UNG to prevent carryover contamination has also been described, see Longo et al. "Use of uracil DNA glycosylase to control carry-over contamination in polymerase chain reaction" (1990) Gene, 93:125-128. State of the art method of controlling carryover contamination using UNG is described in U.S. Pat. Nos. 6,287,823 and 6,518,026 and US 2003/0077637.

Generally, the method involves two steps. First, the PCR assays must include dUTP, so that the amplicons, which are potential carryover contaminants, contain uracil. The method involves substituting dUTP for some or all of the dTTP in the amplification reaction.

Alternatively (or in addition), one or more uracil bases may be incorporated into the amplification primers. It should be noted, however, that if a uracil in the primer is too close to the 5'-end, the method is less efficient at preventing subsequent amplification. The use of dUTP does not interfere with PCR assays. After a uracil-containing amplicon is generated, it can be detected and analyzed by standard methods despite the presence of uracil in place of thymine.

Next, uracil-N-DNA glycosylase is added to a subsequent PCR. Conveniently, UNG is active in a standard reaction mixture that contains all the components of PCR. This enables adding UNG to assembled PCR reactions or even to the PCR master mix. Before the start of thermal cycling, the reaction mixture is incubated at a temperature optimal for the UNG activity within the context of the PCR master mix (about 40° C. to 50° C.) or within the temperature range where UNG is active. If a uracil-containing contaminant from a prior reaction is present, UNG will cleave off the uracil, leaving an abasic site. DNA with abasic sites is known to be labile at high temperature under high pH conditions. When the thermal cycling begins, such DNA is degraded. The high temperature also inactivates the UNG enzyme, allowing generating new DNA amplicons containing uracil.

Particularly applied according to the present invention is the use of an enzyme comprising uracil-DNA glycosylase activity in combination with primers of which at least one forward and/or one reverse primer comprises a polyN tail at the 3' terminus, said tail contains multiple adenine (A) and/or thymine (T) nucleotides and is 2 to 10 nucleotides in length.

Another object of the present invention is a kit for amplifying and detecting a target nucleic acid in a biological sample by any of the methods described above. Said kit comprises at least one enzyme comprising DNA polymerase activity, in particular a thermostable DNA polymerase, at least one enzyme comprising uracil-DNA glycosylase activity, optionally an enzyme comprising transverse transcriptase activity, at least four different nucleoside triphosphates or other nucleoside monomers, at least one polyN extended forward and/or at least one polyN extended reverse primer for generating at least one amplicon, wherein said extended forward primer and/or extended reverse primer comprising a polyN sequence added to the 5' terminus of the primer and being non-complementary to the target sequence, and at least one detectable probe specific for said amplicon or a DNA binding dye as well as a respective buffer. The kit may further comprise reagents for sample preparation, internal control, additional primers and probes, aptamer, detergent and buffer components or the like. Aptamers to be used according to the invention are short, single stranded DNA- or RNA-oligonucleotides (25-70 bases), which bind to a specific molecule (i.e. protein, ZO5 DNA polymerase) through their 3D structure (see e.g. C. Tuerk and L. Gold: Systematic evolution of ligands by exponential enrichment: RNA ligands to bacteriophage T4 DNA polymerase, Science, volume 249, 1990, p. 505-510).

Particularly suited are kits, wherein said polyN sequence comprises a polyA, a polyT, a polyAT, a polyU, a polyC, a polyG sequence being 2 to 10 nucleotides in length. The polyN sequence may be attached to at least one of the primers at the 5' end and may be identical or different in case two or more 5' end extended primers are used. Particular embodiments according to the invention are using primers comprising identical polyN sequences at the 5' end. In particular, polyN sequences comprising four to six consecutive adenine (A) nucleotides are used according to the invention.

EXAMPLES

All experiments were performed under equivalent experimental conditions (i.e., the same master mix compositions, the same primer concentrations, the same sample preparation profiles, the same thermocycling profiles were used and the same amount of amplicons were analyzed per gel). The experiments were therefore conducted as follows: In the master mix the reference primers were substituted by the modified primers according to the present invention. The HPC was generally tested in 5 replicates unless stated otherwise in the Figures and the PCR cycles were terminated after 30, 40, 50, 60 cycles; the amplification products were analyzed on 4% agarose gels.

Example 1

Sample Material

The HPC (high positive control) used for the experiments consisted of high titer samples of about 5E+06 IU/mL comprising armored HCV RNA material in negative human plasma.

The armored RNA consists of non-infectious in vitro transcribed HCV RNA of the target region encapsulated in MS2 bacterial phage coat protein (vendor i.e. Ambion) and contains the HCV primer and probe binding regions. The human plasma was non-reactive for HCV RNA, HIV-1 RNA and HBV DNA.

Nucleic Acid Extraction:

Per reaction 1 mL of sample material was used for nucleic acid extraction. Generally 5 replicates of sample material were tested per experimental condition unless stated otherwise in the Figures. Nucleic acid extraction methods are state-of-the-art and are known by the skilled artisan (see for example Sambrook et al., 2nd Edition 1989, Part 1-3, Molecular Cloning—A Laboratory Manual, Cold Spring Harbor Laboratory, Cold Spring Harbor, N.Y.; Oligonucleotide Synthesis (M. J. Gait, ed., 1984). Alternatively, commercially available nucleic acid extraction kits, i.e. the High Pure Viral Nucleic Acid Kit (Roche Diagnostics) or the COBAS® AmpliPrep Total Nucleic Acid Isolation Kit (TNAI) (Roche Diagnostics) can be used.

In the experiments described here the nucleic acid extraction was based on the COBAS®AmpliPrep Total Nucleic Acid Isolation Kit (TNAI) (Roche Diagnostics). The specimen preparation reagents consist of a magnetic glass particles suspension, a lysis reagent, a protease reagent, an elution buffer and a wash reagent. Quantitation Standard RNA was added to the specimen before nucleic extraction. The armored HCV particles and Quantitation Standard RNA armored particles are lysed by incubation with a protease and a chaotropic lysis/binding buffer that releases nucleic acids and protects the released HCV RNA from RNAses in serum or plasma. Subsequently, the HCV RNA and Quantitation Standard RNA are bound to magnetic glass particles. Unbound substances such as salts, proteins and other cellular impurities are removed by washing the magnetic particles. The adsorbed nucleic acids are eluted at elevated temperature with an aqueous buffer.

Figure 1:
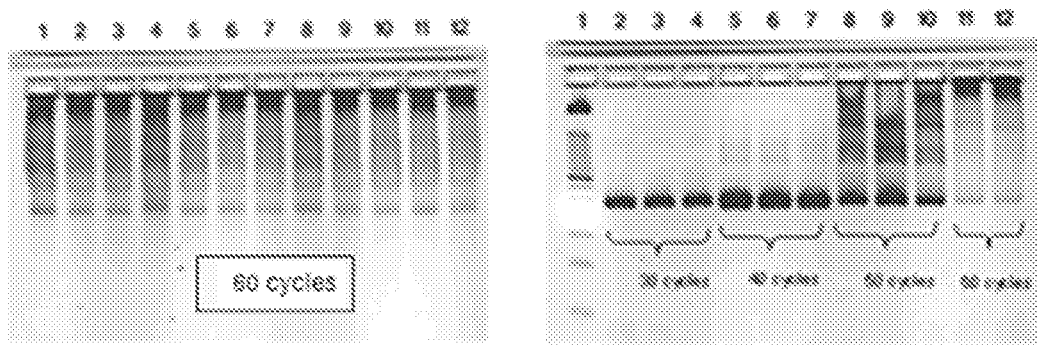
FIG. 1: Result for non-extended reference primers: Formation of high molecular weight products (HMWP, polymerized amplicon, little or no migration into 4% agarose gel) in PCR reactions for high positive control (HPC) after 50 and 60 PCR cycles; agarose gel analysis was carried out on PCR reactions analyzing 12 replicates of HPC after 60 cycles or 3 replicates each after 30, 40, 50 and 60 cycles; primers used: SEQ ID NOS: 1 and 2 (4% agarose gels).
Figure 2:
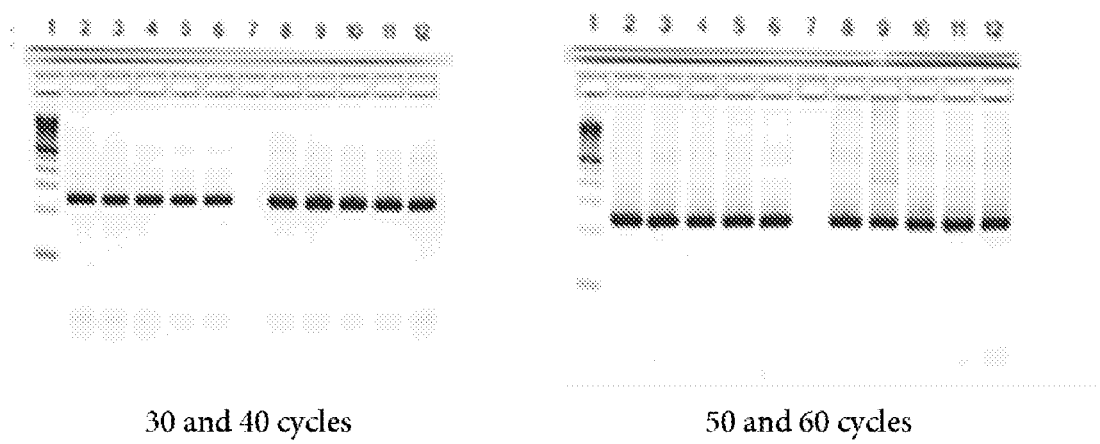
FIG. 2: Result for 5' extended primers with 2 G: significantly reduced HMWP in PCR reactions for high positive control after 30, 40, 50 and 60 cycles; primers used: SEQ ID NOS: 13 and 14, each modified with tert.butylbenzyl (tBu-Bn) at the 3' terminus (4% agarose gels).
Figure 3:
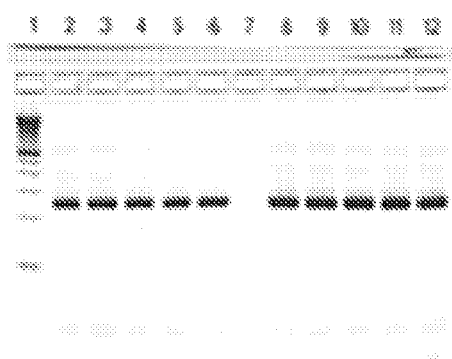
FIG. 3: Result for 5' extended primers with 4 T: significantly reduced HMWP in PCR reactions for high positive control after 30, 40, 50 and 60 cycles; primers used: SEQ ID NOS: 9 and 10, each modified with tert.butylbenzyl (tBu-Bn) at the 3' terminus (4% agarose gels).
Figure 3:
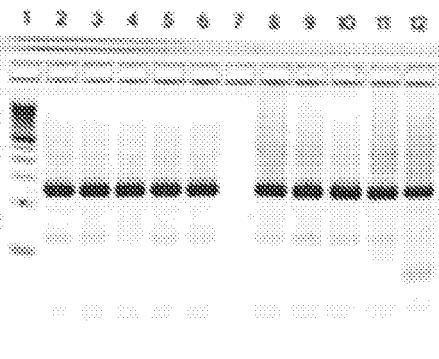
Figure 4:
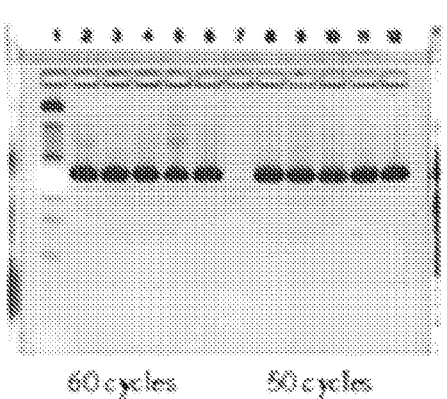
FIG. 4: Result for 5' extended primers with 4 A: No HMWP in PCR reactions for high positive control after 30, 40, 50 and 60 cycles; primers used: SEQ ID NOS: 3 and 4, each modified with tert.butylbenzyl (tBu-Bn) at the 3' terminus (4% agarose gels).
Figure 4:
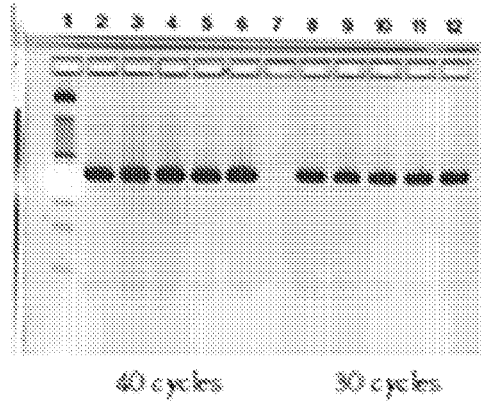
Figure 5:
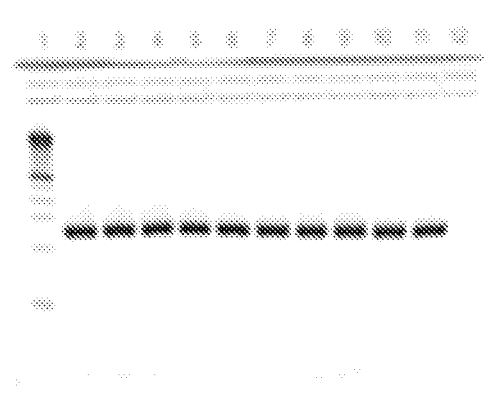
FIG. 5: Result for 5' extended primers with 6 A: No HMWP in PCR reactions for high positive control after 30, 40, 40 and 60 cycles; primers used: SEQ ID NOS: 5 and 6, each modified with tert.butylbenzyl (tBu-Bn) at the 3' terminus (4% agarose gels).
Figure 5:
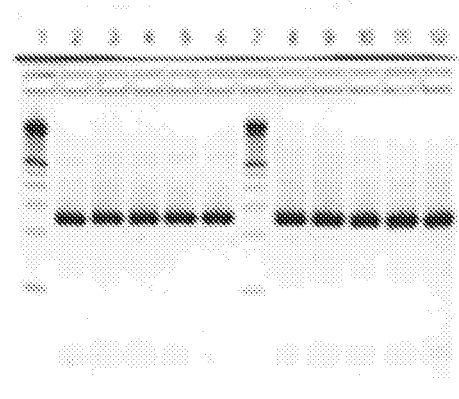
Figure 5:
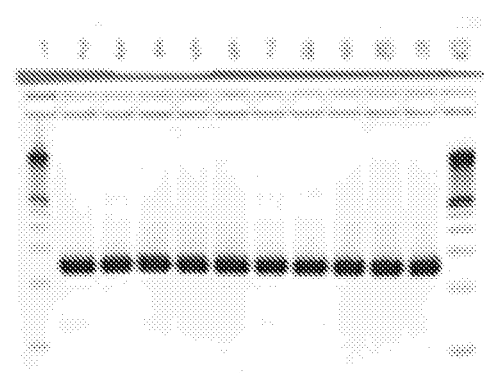
Figure 6:
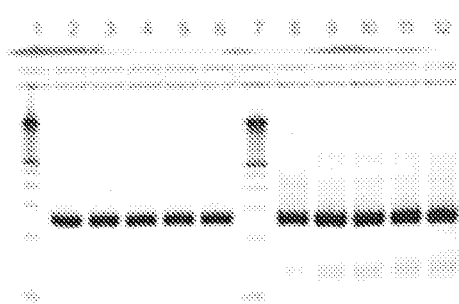
FIG. 6: Result for 5' extended primers with 8 A: No HMWP in PCR reactions for high positive control after 30, 40, 50 and 60 cycles (but slight primer dimer formation); primers used: SEQ ID NOS: 7 and 8, each modified with tert.butylbenzyl (tBu-Bn) at the 3' terminus (4% agarose gels).
Figure 6:
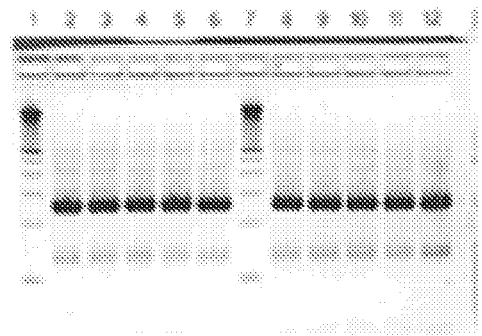
Figure 7:
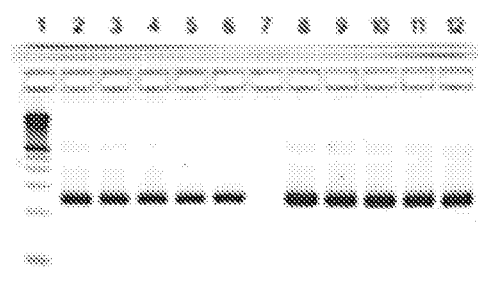
FIG. 7: Result for 5' extended primers with 2 AT: No HMWP in PCR reactions for high positive control after 30, 40, 50 and 60 cycles; primers used: SEQ ID NOS: 15 and 16, each modified with tert.butylbenzyl (tBu-Bn) at the 3' terminus (4% agarose gels).
Figure 7:
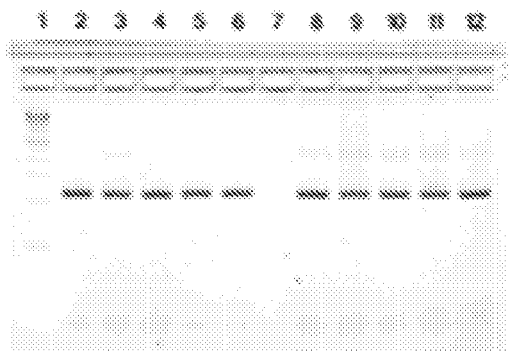
Figure 8:
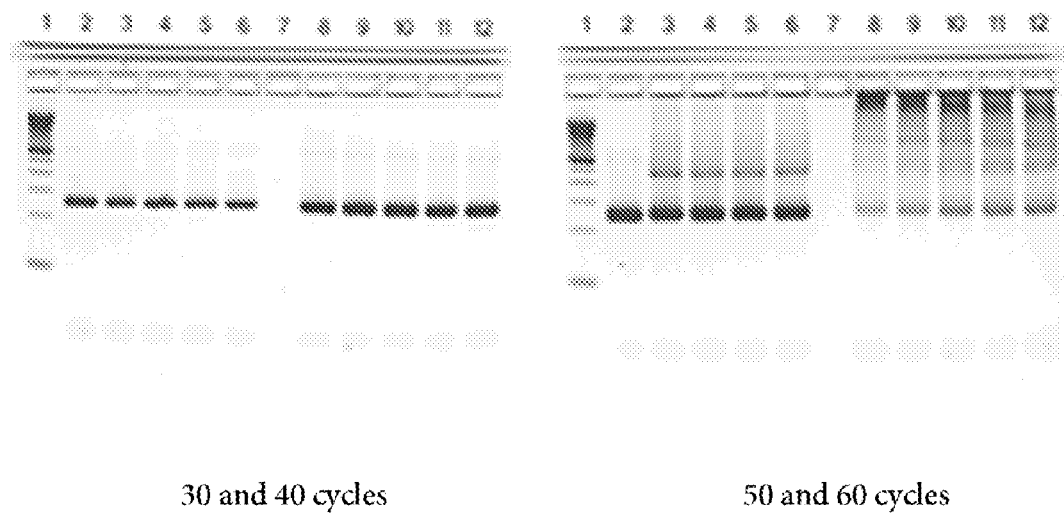
FIG. 8: Result for primers extended at the 5' end with three or four different bases, so-called mixed overhang variants, e.g., GACTTA and CTCTAA, respectively: Minor formation of HMWP in PCR reactions for high positive control after 50 and 60 PCR cycles; agarose gel analysis was carried out on PCR reactions after 30, 40, 50 and 60 cycles; primers used: SEQ ID NOS: 17 and 18, each modified with tert.butylbenzyl (tBu-Bn) at the 3' terminus (4% agarose gels).

PCR Reaction Mixture:

In the master mix the reference primers were substituted by the modified primers according to the present invention. The master mix without the forward and reverse primers was prepared in a large batch. For each experiment this incomplete master mix was supplemented with the extended primers or the reference primers as specified in the FIGS. 1-8.

TABLE 1

Master mix composition

| Chemical | Concentration |
| --- | --- |
| Tricine | 157 mM |
| Potassium acetate | 314 mM |
| DMSO | 15.8% |
| Sodium Azide | 0.09% |
| Glycerol | 14.4% |
| Potassium Hydroxide | 36.9 mM |
| dNTPs (dATP, dCTP, dGTP, dUTP) | 1.29 mM each |
| Forward primer (SEQ ID NOS: 1, 3, 5, 7, 9, 13, 15 or 17)* | 2.14 µM |
| Reverse primer (SEQ ID NOS: 2, 4, 6, 8, 10, 14, 16 or 18)* | 2.14 µM |
| Second reverse primer (SEQ ID NO: 32) | 1.07 µM |
| Target probe (SEQ ID NOS: 27, 28, 29 and/or 30) | 428 nM |
| QS probe (SEQ ID NO: 31) | 428 nM |
| Z05 polymerase | 1142 KU/L |
| UNG | 114 KU/L |
| Aptamer | 572 nM |
| pH | 7.8 |

*different in each experiment.

50 µL of nucleic acid containing eluate were added to 35 µL of master mix and 15 µL of 18 mM manganese acetate in PCR tubes and loaded onto the COBAS® TaqMan® 48 Analyzer.

PCR Reaction:

TABLE 2

The thermal cycling steps applied

| Duration | Temperature | Repetitions |
| --- | --- | --- |
| 5 min | 50° C. | 1 |
| 30 min | 66° C. | 1 |
| 15 sec | 95° C. | 30 to 60* |
| 25 sec | 58° C. | 30 to 60* |
| 2 min | 40° C. | 1 |

*per experiment PCR was terminated after 30, 40, 50 and 60 cycles as shown in FIGS. 1-8, respectively.

Agarose Gel Analysis:

Agarose gel analysis was performed as known by the skilled artisan (see for example Sambrook et al., 2nd Edition 1989, Part 1-3, Molecular Cloning—A Laboratory Manual, Cold Spring Harbor Laboratory, Cold Spring Harbor, N.Y.; Oligonucleotide Synthesis (M. J. Gait, ed., 1984). 5 µL of amplicon were mixed with 5 µL of agarose gel loading buffer and applied to 4% agarose gels. DNA was visualized under UV after ethidium bromide staining. The resulting photographs are shown in FIGS. 1 to 8 below.

Example 2

The results presented are also achieved by the following procedure: Commercially available assays, e.g., COBAS® AmpliPrep/COBAS® TaqMan® HCV Test (manufactured by Roche Diagnostics), are used for extracting HCV RNA from the high positive kit control. Specimen preparation is automated using the COBAS® AmpliPrep Instrument and amplification/detection is automated using, e.g., the COBAS® TaqMan® Analyzer or the COBAS® TaqMan® 48 Analyzer. The test is based on three major processes: (1) specimen preparation to isolate RNA from human EDTA plasma or serum and controls which are provided in secondary tubes on the COBAS® AmpliPrep Instrument; (2) reverse transcription of the target RNA and the Quantitation Standard/Internal Control RNA to generate complementary DNA (cDNA) and (3) PCR amplification of target cDNA and Quantitation Standard/Internal Control cDNA with simultaneous detection of the generated amplicons on the COBAS® TaqMan® Analyzer by cleavage of dual-labeled detection probes specific to the target and to the Quantitation Standard/Internal Control.

The specimen preparation reagents consist of a magnetic glass particles suspension, a lysis reagent, a protease reagent, an elution buffer and a wash reagent. The HCV particles as well as the Quantitation Standard/Internal Control particles are lysed by incubation with a protease and a chaotropic lysis/binding buffer that releases nucleic acids and protects the released HCV RNA from RNAses in serum or plasma. Subsequently, the HCV RNA and Quantitation Standard RNA are bound to magnetic glass particles. Unbound substances such as salts, proteins and other cellular impurities are removed by washing the magnetic particles. The adsorbed nucleic acids are eluted at elevated temperature with an aqueous buffer. The specimen or control eluate is added to the master mix and transferred to the COBAS® TaqMan Analyzer® or the COBAS® TaqMan® 48 Analyzer for amplification and detection.

For the experiments presented here, the COBAS® AmpliPrep/COBAS® TaqMan® HCV Test master mix is modified with the extended primers according to the information given below and the reagent cassette with the modified master mix is used on the COBAS®AmpliPrep instrument. The master mix contains primer and probe pairs specific for both HCV RNA and Quantitation Standard/Internal Control RNA. The primer binding sites are shared by the HCV target and the Quantitation Standard/Internal Control. Primers and target probe are located in a highly conserved part of the 5'-untranslated region of the HCV genome. The detection of HCV target and Quantitation Standard is performed using a target-specific and a Quantitation Standard-specific dual-labeled oligonucleotide probe which permits independent identification of HCV target amplicon and HCV Quantitation Standard amplicon. The HCV Quantitation Standard is automatically added to each specimen at a known copy number by the COBAS® AmpliPrep and is carried through the entire specimen preparation, reverse transcription, amplification and detection steps along with the HCV target. The Quantitation Standard must give a positive signal in HCV target negative and positive specimens in order to enable titer determination. In partly suppressed or inhibited reactions the Quantitation Standards is affected similarly as the target and thus allows correct titer determination. Finally, the Quantitation Standard monitors HCV target negative reactions for inhibitory effects but due to its rather high concentration monitoring is not stringent.

TABLE 3

Master mix composition

| Chemical | Concentration |
| --- | --- |
| Tricine | 157 mM |
| Potassium acetate | 314 mM |
| DMSO | 15.8% |
| Sodium Azide | 0.09% |
| Glycerol | 14.4% |
| Potassium Hydroxide | 36.9 mM |
| dNTPs (dATP, dCTP, dGTP, dUTP) | 1.29 mM each |
| Forward primer (SEQ ID NOS: 1, 3, 5, 7, 9, 13, 15 or 17)* | 2.14 µM |
| Reverse primer (SEQ ID NOS: 2, 4, 6, 8, 10, 14, 16 or 18)* | 2.14 µM |
| Second reverse primer (SEQ ID NO: 32) | 1.07 µM |
| Target probe (SEQ ID NOS: 27, 28, 29 and/or 30) | 428 nM |
| QS probe (SEQ ID NO: 31) | 428 nM |
| ZO5 polymerase | 1142 KU/L |
| UNG | 114 KU/L |
| Aptamer | 572 nM |
| pH | 7.8 |

*different in each experiment.

The master mix without the forward and reverse primers is prepared in a large batch. For each experiment this incomplete master mix is supplemented with the extended primers as shown in the graphs. These supplemented master mix variations are filled into reagent cassettes and are loaded onto the COBAS® AmpliPrep.

The HPC of the COBAS® AmpliPrep/COBAS® TaqMan® HCV Test Kit is tested as sample. The automated process for the extraction and amplification/detection is started on the COBAS® AmpliPrep/COBAS® TaqMan®. As needed, PCR is stopped after 30, 40, 50 or 60 cycles and 5 µL of amplification product are analysed on 4% agarose gels.

It is understood that the examples and embodiments described herein are for illustrative purposes only and that various modifications or changes in light thereof will be suggested to persons skilled in the art.

The invention claimed is:

1. A method for amplifying and detecting a target nucleic acid of HCV in a biological sample suspected of containing the target nucleic acid, said method comprising:
   a) contacting nucleic acids in said biological sample with amplification reagents comprising at least a DNA polymerase, nucleoside triphosphate monomers, at least one extended forward primer specific for said target nucleic acid, or at least one extended reverse primer specific for said target nucleic acid, or a combination thereof, for generating at least one amplicon, and at least one detectable probe specific for said amplicon, or at least one DNA binding dye, wherein said at least one extended forward primer or said at least one reverse primer comprises a polyN sequence of between 2 and 10 nucleotides in length added to the 5' terminus of the primer, said polyN sequence being non-complementary to the target sequence and comprising 100% of either (i) one defined selected nucleotide or (ii) two defined selected nucleotides, wherein said primer is sufficiently complementary to hybridize with said target nucleic acid,
   b) incubating said nucleic acids with said amplification reagents for a period of time and under conditions sufficient for an amplification reaction to occur, wherein the formation of high molecular weight products during amplification is reduced as compared to amplification without a primer comprising a polyN sequence; and
   c) detecting said amplicon via said at least one detectable probe or said at least one DNA binding dye.

2. The method according to claim 1, wherein said polyN sequence comprises a polyA, a polyT, a polyAT, a polyU, a polyC or a polyG sequence.

3. The method according to claim 1, wherein said polyN sequence is between 4 to 6 nucleotides in length.

4. The method according to claim 1, wherein said amplification reaction terminates after at least 50 cycles.

5. The method according to claim 1, wherein at least step b) is performed in the presence of an enzyme comprising uracil-DNA glycosylase activity.

6. The method according to claim 1, wherein said at least one extended forward primer comprises a sequence from the group consisting of SEQ ID NO:3, SEQ ID NO: 5, SEQ ID NO: 7, SEQ ID NO: 9, SEQ ID NO: 11, SEQ ID NO: 13, SEQ ID NO:15, SEQ ID NO:19, SEQ ID NO: 21, and SEQ ID NO: 23.

7. The method according to claim 1, wherein said at least one detectable probe comprises a sequence from the group consisting of SEQ ID NO: 27, SEQ ID NO: 28, SEQ ID NO: 29, SEQ ID NO: 30 and the complementary sequences thereof.

8. The method according to claim 1, wherein said at least one extended reverse primer comprises a sequence from the group consisting of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 20, and SEQ ID NO: 22.

9. The method according to claim 1, wherein said at least one extended reverse primer comprises SEQ ID NO: 4, and wherein said at least one extended forward primer comprises SEQ ID NO: 3.

10. The method according to claim 1, wherein said at least one extended reverse primer comprises SEQ ID NO: 6, and wherein said at least one extended forward primer comprises SEQ ID NO: 5.

11. The method according to claim 1, wherein said at least one extended reverse primer comprises SEQ ID NO: 8, and wherein said at least one extended forwarded primer comprises SEQ ID NO: 7.

12. The method according to claim 1, wherein said at least one extended reverse primer comprises SEQ ID NO: 10, and wherein said at least one extended forwarded primer comprises SEQ ID NO: 9.

13. The method according to claim 1, wherein said at least one extended reverse primer comprises SEQ ID NO: 14, and wherein said at least one extended forwarded primer comprises SEQ ID NO: 13.

14. The method according to claim 1, wherein said at least one extended reverse primer comprises SEQ ID NO: 16, and wherein said at least one extended forwarded primer comprises SEQ ID NO: 15.

15. The method according to claim 1, wherein said at least one detectable probe comprises SEQ ID NO: 29 or the complementary sequence thereof.

16. The method according to claim 3, wherein said polyN sequence is between 4 to 6 consecutive adenine (A) nucleotides in length.

17. The method according to claim 1, wherein said at least one extended reverse primer comprises SEQ ID NO: 12, and wherein said at least one extended forward primer comprises SEQ ID NO: 11.

* * * * *